US008569374B2

(12) United States Patent
Veasey

(10) Patent No.: US 8,569,374 B2
(45) Date of Patent: Oct. 29, 2013

(54) NADPH OXIDASE INHIBITION PHARMACOTHERAPIES FOR OBSTRUCTIVE SLEEP APNEA SYNDROME AND ITS ASSOCIATED MORBIDITIES

(75) Inventor: Sigrid C. Veasey, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 1786 days.

(21) Appl. No.: 11/226,471

(22) Filed: Sep. 15, 2005

(65) Prior Publication Data

US 2006/0154856 A1 Jul. 13, 2006

Related U.S. Application Data

(60) Provisional application No. 60/610,428, filed on Sep. 16, 2004.

(51) Int. Cl.
*A61K 31/19* (2006.01)
*C12N 15/11* (2006.01)

(52) U.S. Cl.
USPC ........................................ 514/568; 514/44 A

(58) Field of Classification Search
USPC ................................................ 514/568, 44 A
See application file for complete search history.

(56) References Cited

U.S. PATENT DOCUMENTS

| 5,902,831 | A | 5/1999 | Holland et al. | |
|---|---|---|---|---|
| 6,090,851 | A * | 7/2000 | Dodd-o et al. | 514/568 |
| 2003/0199482 | A1 * | 10/2003 | Seibert et al. | 514/171 |
| 2004/0001818 | A1 | 1/2004 | Aird et al. | |
| 2004/0259247 | A1 | 12/2004 | Tuschl et al. | |

FOREIGN PATENT DOCUMENTS

| EP | 0322464 | 9/1989 |
|---|---|---|
| JP | 7313180 | 12/1995 |
| WO | WO/94/14950 | 7/1994 |
| WO | WO/97/19679 | 6/1997 |
| WO | WO/02/30453 A1 | 4/2002 |

OTHER PUBLICATIONS

Schluter et al. (2009) Cardiovascular Research (2008) 80, 271-279.*
Lavie (2003) Sleep Med. Rev. 7(1):35-51.*
Elbashir et al. (2002) Methods 26:199-213.*
Abramov AY. Canevari L. Duchen MR. Beta-amyloid peptides induce mitochondrial dysfunction and oxidative stress in astrocytes and death of neurons through activation of NADPH oxidase. Journal of Neuroscience. 24(2):565-75, 2004.
Alberti, A., Sarchielli, P., Gallinelia, E., Floridi, A., Mazzotta, G., and Gallai, V. 2003. Plasma cytokine levels in patients with obstructive sleep apnea syndrome: a preliminary study. / Sleep Res 12:305-311.
Bataller, R., Schwabe, R.F., Choi, Y.H., Yang, L., Paik, Y.H., Linciquist, J., Qian, T., Schoonhoven, R., Hagedorn, C.H., Lemasters, J.J., et al. 2003. NADPH oxidase signal transduces angiotensin II in hepatic stellate cells and is critical in hepatic fibrosis. J Clin Invest 112:1383-1394.
Bruck, R., Aeed, H., Shirin, H., Matas, Z., Zaidel, L., Avni, Y., and Halpern, Z. 1999. The hydroxyl radical scavengers dimethylsulfoxide and dimethylthiourea protect rats against thioacetamide-induced fulminant hepatic failure. J Hepatol 31:27-38.
Carpagnano GE, et al "8-Isoprostane, a marker of oxidative stress, is increased in exhaled breath condensate of patients with obstructive sleep apnea after night and is reduced by continuous positive airway pressure therapy." Chest 2003 124:1386-1392.
Del Villar, K., and Miller, C.A. 2004. Down-regulation of DENN/MADD, a TNF receptor binding protein, correlates with neuronal cell death in Alzheimer's disease brain and hippocampal neurons. Proc Natl Acad Sci USA 101:4210-4215.
Diekmann D. Abo A Johnston C Segal A.W. and Hall A. 1994. Interaction of Rac with p67phox and regulation of phagocytic NADPH oxidase activity. Science 265:531-533.
Douglas, N.J., and Engleman, H.M. 2000. Effects of CPAP on vigilance and related functions in patients with the sleep apnea/hypopnea syndrome. Sleep 23 Suppl 4:S147-149.
Franken, P., Chollet, D., and Tafti, M. 2001. The homeostatic regulation of sleep need is under genetic control. / Neurosci 21:2610-2621.
Gao, H.M., Hong, J.S., Zhang, W., and Liu, B. 2003. Synergistic dopaminergic neurotoxicity of the pesticide rotenone and inflammogen lipopolysaccharide: relevance to the etiology of Parkinson's disease. J Neurosci 23:1228-1236.
Gow, A.J., McClelland, M., Garner, S.E., Malcolm, S., and Ischiropoulos, H. 1998. The determination of nitrotyrosine residues in proteins. Methods Mol Biol 100:291-299.
Gozal, D., Daniel, J.M., andDohanich, G.P. 2001. Behavioral and anatomical correlates of chronic episodic hypoxia during sleep in the rat. J Neurosci 21:2442-2450.
Gu, X.Q., and Haddad, G.G. 2001. Decreased neuronal excitability in hippocampal neurons of mice exposed to cyclic hypoxia. J Appl Physiol 91:1245-1250.
Hebert, G., Arsaut, J., Dantzer, R., and Demotes-Mainard, 1 2003. Time-course of the expression of inflammatory cytokines and matrix rnetailoproteinases in the striatum and mesencephalon of mice injected with 1-methyl-4-phenyl-I,2,3,6-tetrahydropyridine, a dopaminergic neurotoxin. Neurosci Lett 349:191-195.
Hitomi, Y., Miyamura, M., Mori, S., Suzuki, K., Kizaki, T., Itoh, C, Murakami, K., Haga, S., and Ohno, H. 2003. Intermittent hypobaric hypoxia increases the ability of neutrophils to generate superoxide anion in humans. Clin Exp Pharmacol Physiol 30:659-664.
Iles, K.E., andForman, HJ. 2002. Macrophage signaling and respiratory burst. Immunol Res 26:95-105.
Kono, H., Rusyn, L, Yin, M., Gabele, E., Yamashina, S., Dikalova, A., Kadiiska, M.B., Connor, H.D., Mason, R.P., Segal, B.H., et al. 2000. NADPH oxidase-derived free radicals are key oxidants in alcohol-induced liver disease. 3 Clin Invest 106:867-872.
Lavie, L., Vishnevsky, A., and Lavie, P. 2004. Evidence for lipid peroxidation in obstructive sleep apnea. Sleep 27:123-128.
Li, R., Yang, L., Lindholm, K., Konishi, Y., Yue, X., Hampel, H., Zhang, D., and Shen, Y. 2004. Tumor necrosis factor death receptor signaling cascade is required for amyloid-beta protein-induced neuron death. J Neurosci 24:1760-1771.

(Continued)

*Primary Examiner* — J E Angell
(74) *Attorney, Agent, or Firm* — Mark S. Cohen; Pearl Cohen; Zedek Latzer Baratz LLP

(57) ABSTRACT

The invention relates to compositions and methods for treating Obstructive Sleep Apnea (OSA). Specifically, the invention relates to the use of NADPH Oxigenase inhibitors in compositions and methods for treating OSA in a subject.

7 Claims, 6 Drawing Sheets

(56) References Cited

OTHER PUBLICATIONS

Lim, G.P., Chu, T., Yang, F., Beech, W., Frautschy, S.A., and Cole, G.M. 2001. The curry spice curcumin reduces oxidative damage and amyloid pathology in an Alzheimer transgenic mouse. J Neurosci 21:8370-8377.

Schroeter, M., Kury, P., and Jander, S. 2003. Inflammatory gene expression in focal cortical brain ischemia: differences between rats and mice. Brain Res Mol Brain Res 117:1-7.

Veasey S.C., Days, C.W., Fenik, P., Zhan, G., Hsu, Y.J., Pratico, D., and Gow, A. 2004. Long-term, intermittent hypoxia in mice: protracted hypersomnolence with, oxidative injury to sleep-wake brain regions. Sleep 27:194-201.

Cai et al (2003) "The Vascular NAD(P)H Oxidases as Therapeutic Targets in Cardiovascular Diseases" Trends Pharmocol Sci 24:471.

Zhan et al (2005) "NADPH Oxidase Mediates Hypersomnolence and Brain Oxidative Injury in a Murine Model of Sleep Apnea" Am J. Resp Crit Care Med 172:921.

Shimohama S et al. "Activation of NADPH oxidase in Alzheimer's disease brains." Biochem Biophys Res Commun. Jun. 24, 2000;273(1):5-9.

Gao HM et al. "Critical role for microglial NADPH oxidase in rotenone-induced degeneration of dopaminergic neurons." J Neurosci. Jul. 16, 2003;23(15):6181-7.

\* cited by examiner

SEQUENCE LISTING

<160> NUMBER OF SEQ ID NOS: 12

<210> SEQ ID NO 1
<211> LENGTH: 18
<212> TYPE: DNA
<213> ORGANISM: Murine

<400> SEQUENCE: 1
cgctctcgcc agaacaca                    18

<210> SEQ ID NO 2
<211> LENGTH: 20
<212> TYPE: DNA
<213> ORGANISM: Murine

<400> SEQUENCE: 2

-continued

```
ttggtcaccc accgtatgct                                           20

<210> SEQ ID NO 3
<211> LENGTH: 20
<212> TYPE: DNA
<213> ORGANISM: Murine

<400> SEQUENCE: 3
ctaccggcgt cgggacagcc                                           20

<210> SEQ ID NO 4
<211> LENGTH: 22
<212> TYPE: DNA
<213> ORGANISM: Murine

<400> SEQUENCE: 4
ccaggttctc ttcaagggac aa                                        22

<210> SEQ ID NO 5
<211> LENGTH: 21
<212> TYPE: DNA
<213> ORGANISM: Murine

<400> SEQUENCE: 5
cggcagagag gaggttgact t                                         21

<210> SEQ ID NO 6
<211> LENGTH: 21
<212> TYPE: DNA
<213> ORGANISM: Murine

<400> SEQUENCE: 6
cctcacccac accgtcagcc g                                         21

<210> SEQ ID NO 7
<211> LENGTH: 20
<212> TYPE: DNA
<213> ORGANISM: Murine

<400> SEQUENCE: 7
caggagatgg tccgcaagag                                           20

<210> SEQ ID NO 8
<211> LENGTH: 23
<212> TYPE: DNA
<213> ORGANISM: Murine

<400> SEQUENCE: 8
aatttctgca gccatttcct tct                                       23

<210> SEQ ID NO 9
<211> LENGTH: 21
<212> TYPE: DNA
<213> ORGANISM: Murine

<400> SEQUENCE: 9
tgcacacagg ctactcccgg c                                         21

<210> SEQ ID NO 10
<211> LENGTH: 22
<212> TYPE: DNA
<213> ORGANISM: Murine

<400> SEQUENCE: 10
```

```
tccattgacc agagcagaga ga                                              22

<210> SEQ ID NO 11
<211> LENGTH: 23
<212> TYPE: DNA
<213> ORGANISM: Murine

<400> SEQUENCE: 11
aatttctgca gccatttcct tct                                             23

<210> SEQ ID NO 12
<211> LENGTH: 24
<212> TYPE: DNA
<213> ORGANISM: Murine

<400> SEQUENCE: 12
ttctccctga agccgtacac atca                                            24
```

NADPH OXIDASE INHIBITION PHARMACOTHERAPIES FOR OBSTRUCTIVE SLEEP APNEA SYNDROME AND ITS ASSOCIATED MORBIDITIES

CROSS REFERENCE TO RELATED APPLICATIONS

This application claims benefit of U.S. Provisional application No. 60/610,428, filed Sep. 16, 2004.

FIELD OF INVENTION

This invention relates to methods and compositions used for treating Obstructive Sleep Apnea (OSA). Specifically, the invention relates to the use of NADPH Oxigenase inhibitors in compositions and methods for treating OSA in a subject.

BACKGROUND OF THE INVENTION

Obstructive sleep apnea (OSA) with daytime hypersomnolence is present in at least 2-4% of adults in developed countries. OSA may affect more than 50% of individuals over the age of 65, and significant depressive symptoms may be present in as many as 26% of a community-dwelling population of older adults. This disorder manifests as repeated events of sleep state-dependent reductions in upper airway dilator motoneuronal activity with consequent upper airway occlusions and oxyhemoglobin desaturations, each terminating with abrupt arousal and reoxygenation. The hypoxia and reoxygenation events may occur as frequently as once every minute of sleep. Despite therapy to alleviate obstructive sleep apnea events, many individuals with OSA have residual sleepiness. Mechanisms of the residual hypersomnolence in persons with OSA are not understood, but severity of hypoxemia in OSA predicts, in part, severity of hypersomnolence.

Long-term intermittent hypoxia in mice, modeling the patterns of hypoxia/reoxygenation observed in moderate-severe sleep apnea, results in protracted hypersomnolence and hippocampus-dependent memory impairments with significant oxidative modifications in many brain regions, including wake-active regions and the hippocampus. The oxidative modifications observed following hypoxia/reoxygenation in wake-active neural groups that might contribute to impaired wakefulness and hypersomnolence include nitration, lipid peroxidation and carbonylation (7, 8, 12). Inducible nitric oxide synthase (iNOS) contributes to nitration and lipid peroxidation injuries in the intermittent hypoxia model of sleep apnea; however, transgenic absence of iNOS function does not confer resistance to intermittent hypoxia carbonylation injury and bestows only partial resistance on the proinflammatory gene response. A source of oxidation injury from long-term hypoxia/reoxygenation should be identified.

NADPH oxidase-dependent production of superoxide radical ($O_2^-$.) has been identified as a major contributor to oxidative injury in the brain under conditions of both inflammation and severe hypoxia/reperfusion injury. Moreover, NADPH oxidase has been implicated in oxidative neurodegeneration, including Alzheimer's disease and in dopaminergic neuronal injury in murine models of Parkinson's disease. NADPH oxidase has been identified in select populations of neurons, raising the possibility that neuronal NADPH oxidase activation could contribute to enhanced neuronal vulnerability to oxidative injury. Presently, it is unknown whether NADPH oxidase is present in wake-active neurons, whether intermittent hypoxia that models sleep apnea increases NADPH oxidase in regions with wake-active neurons, or whether NADPH oxidase might mediate the intermittent hypoxia-induced hypersomnolence, oxidative injury and/or proinflammatory responses.

SUMMARY OF THE INVENTION

In one embodiment the invention provides a method for treating a morbidity resulting from Obstructive Sleep Apnea (OSA) hypopnea syndrome in a subject, comprising administering to said subject a therapeutically effective amount of a composition comprising an NADPH Oxidase inhibitor, thereby treating said morbidity.

In another embodiment, the invention provides a method for treating a neurobehavioral morbidity resulting from Obstructive Sleep Apnea (OSA) hypopnea syndrome in a subject, comprising administering to said subject a therapeutically effective amount of a composition comprising an NADPH Oxidase inhibitor, thereby treating said morbidity.

In one embodiment, the invention provides a method for treating a cardiovascular morbidity resulting from Obstructive Sleep Apnea (OSA) hypopnea syndrome in a subject, comprising administering to said subject a therapeutically effective amount of a composition comprising an NADPH Oxidase inhibitor, thereby treating said morbidity In another embodiment, the invention provides a composition comprising at least two of an NADPH Oxidase inhibitor, a siRNA of $p67^{phox}$, a siRNA of $p47^{phox}$, a siRNA of $gp91^{phox}$, COX-2 Inhibitor or a combination thereof.

In one embodiment, the invention provides a method of treating brain oxidative injury, microglial activation or proinflammatory gene expression, induced by long-term intermittent hypoxia (LTIH) in a region of the brain, comprising contacting said cell with a composition comprising NADPH Oxigenase inhibitor.

In another embodiment, the invention provides a method for predicting the probability of developing hypoxia/reoxygenation proinflammatory nuronal injury in a subject, comprising obtaining a nuronal cell from a subject; and analyzing said nuronal cell for the presence of NADPH Oxigenase wherein presence of NADPH Oxidase indicates vulnerability to hypoxia/reoxygenation proinflammatory nuronal injury.

DETAILED DESCRIPTION OF THE INVENTION

Figure 1:
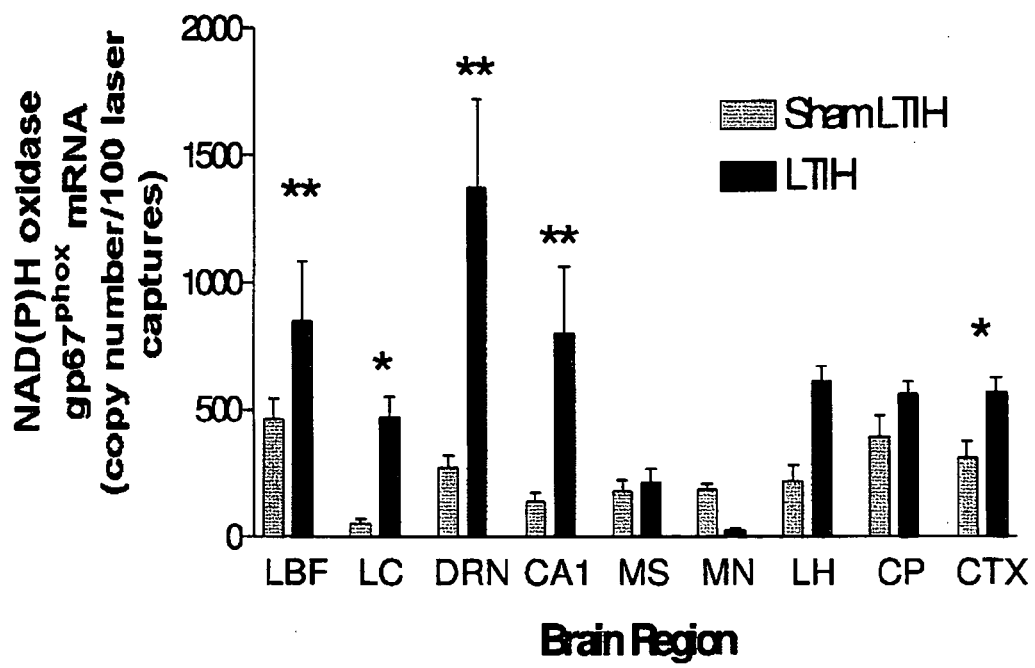
FIG. 1. Long-term intermittent hypoxia, modeling oxygenation patterns in sleep apnea, results in increased NADPH oxidase gene and protein expression in wake-active brain regions. A) NADPH oxidase subunit $p67^{phox}$ mRNA was measured in laser-captured neurons in brain regions selected because of behavioral state-dependency or known hypoxia-sensitivity. Taqman RT-PCR was performed on 50 laser-captured neurons each the following brain regions: LBF, lateral basal forebrain (magnocellular preoptic, horizontal diagonal band and substantia inominata); LC, locus coeruleus; DRN, dorsal raphe nucleus; CA1, hippocampal CA1 pyramidal cells; MS, medial septum/vertical diagonal band; MP, median preoptic area; LH, perifornicular lateral hypothalamus; STR, striatum; and CTX, cortex. Comparison were drawn between wild type mice exposed to LTIH and sham LTIH (n=10), Asterisks: (*) denotes p<0.05 and (**) denote p<0.001. B). NADPH oxidase subunit $p47^{phox}$ immunoreactivity (47 kDa) in locus coeruleus and lateral basal forebrain micropunches in adult mice following LTIH and sham LTIH, revealed increased $p47^{phox}$ in mice exposed to LTIH, Asterisk denotes p<0.01 in matched regions.
Figure 1:
Figure 1:
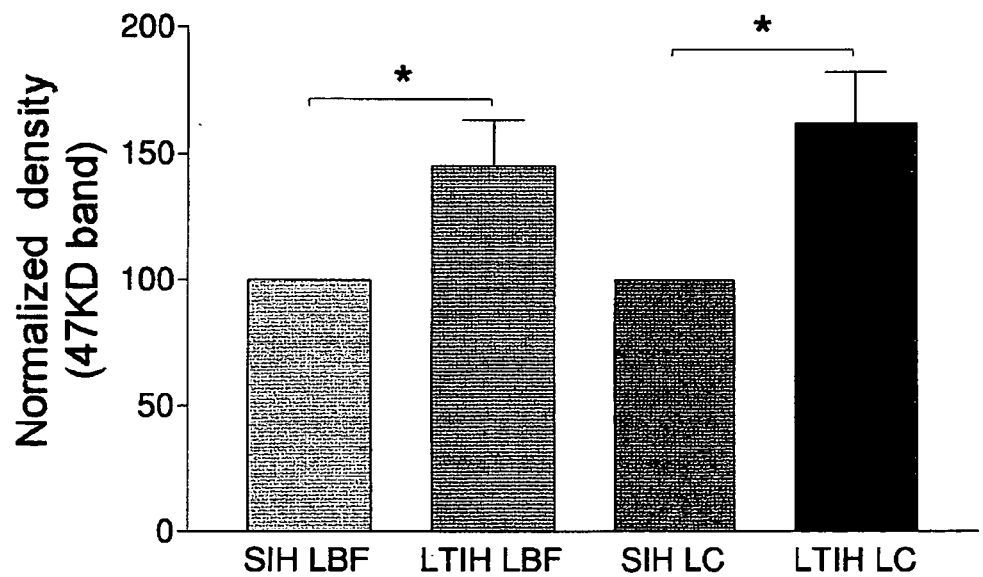

Frequent hypoxia/reoxygenation events, which replicate oxygenation patterns in sleep apnea, induce in one embodiment NADPH oxidase and proinflammatory gene expression in select brain regions, including in another embodiment, in wake-active neurons. In one embodiment, lack of a functional NADPH oxidase and pharmacological inhibition of NADPH oxidase is determined to confer resistance to intermittent hypoxia-induced neurobehavioral, redox and pro-inflammatory changes, thereby emphasizing a potential target to prevent oxidative morbidities in persons with obstructive sleep apnea (OSA).

OSA is a form of sleep disordered breathing (SDB) and is defined by frequent episodes of obstructed breathing during sleep. In one embodiment, it is characterized by sleep-related decreases (hypopneas) or pauses (apneas) in respiration. In one embodiment, obstructive apnea is defined as at least 10 seconds interruption of oronasal airflow, corresponding to a complete obstruction of the upper airways, despite continuous chest and is abdominal movements, and is associated in another embodiment, with a decrease in oxygen saturation or arousals from sleep. In one embodiment, obstructive hypopnea is defined as at least 10 seconds of partial obstruction of the upper airways, resulting in an at least 50% decrease in oronasal airflow.

Cheyne-Stokes respiration (CSR) is by far the most common form of SDB encountered with an estimated prevalence of 40% (Javaheri et al., 1995, Ann Intern Med., 122:487-92; Findley et al., 1985, South Med. J., 78:11-5). It is characterized in one embodiment, by rhythmic rises and falls in tidal volume and breathing frequency that lead to oxygen desaturation, increased arousals, poor sleep quality, or and altered sleep architecture in other embodiments. These features result in neurobehavioral morbidities, such as in one embodiment daytime somnolence, or fatigue, and insomnia in other embodiments. IN one embodiment, the methods and compositions of the invention are used to treat a subject having the Cheyne-Stokes respiration form of SDB.

In one embodiment, the effect of altered breathing patterns may extend beyond the deterioration in psycho-cognitive function. The increase in one embodiment, in urinary and plasma norepinephrine levels in patients with left ventricular failure (LVF) and CSR compared to those with CSR alone has been implicated in an accelerated loss of cardiac function, and serve as an example of associated cardiovascular morobidity treated by the methods and compositions of the invention; and an increased risk of death and cardiac transplantation (Naughton et al., 1995, Am J Respir Crit Care Med, 152:473-

79; Hanly et al., 1996, Am J Respir Crit Care Med, 153:272-76). In one embodiment, Nasal continuous positive airway pressure (CPAP) is an effective nonpharmacological treatment for patients with congestive heart failure and CSR. Recent studies have shown that CPAP can abolish CSR, improve respiratory muscle strength (Granton et al., 1996, Am J Respir Crit Care Med, 153:277-82), and increase left ventricular ejection fraction (Naughton et al., 1993, Am Rev Respir Dis, 148:330-38), and may increase transplant-free survival In one embodiment, CPAP may be used in conjunction with the methods and compositions of the invention.

In one embodiment, a selective vulnerability to hypoxia/reoxygenation neuronal proinflammatory injury, can be predicted by whether NADPH oxidase is present in the neurons. In another embodiment NADPH oxidase plays a critical role in sleep apnea-induced hypoxia/reoxygenation injury in other physiological systems, including in one embodiment, cardiovascular functions. Thus, NADPH oxidase and its downstream effector pathways should be considered molecular targets for pharmacological and therapeutic intervention for the treatment or prevention of oxidative mediated cardiovascular and neurobehavioral morbidities of obstructive sleep apnea.

According to this aspect of the invention and in one embodiment, the invention provides a method for treating a cardiovascular morbidity, a neurobehavioral morbidity or a combination thereof, resulting from Obstructive Sleep Apnea (OSA) hypopnea syndrome in a subject, comprising administering to said subject a therapeutically effective amount of a composition comprising an NADPH Oxidase inhibitor.

NADPH oxidase is increasingly recognized for its dual-edge roles in health and disease, necessary for normal immunity and cell signaling, yet critical in the pathogenesis of diverse morbid conditions, including. Alzheimer's disease, Parkinson's disease, and cardiovascular disease. In one embodiment, expression of several NADPH oxidase proteins is increased in a population of wake-active neurons, under conditions of long-term hypoxia/reoxygenation events replicating in another embodiment, the oxygenation patterns observed in persons with moderate-severe obstructive sleep apnea. In one embodiment, the NADPH oxidase response to long-term hypoxia/reoxygenation is detrimental to brain function. In another embodiment, oxidase plays an essential role in, not only in the hypersomnolence and increased sleep propensity associated with the hypoxia/re-oxygenation model of sleep apnea, but also in the associated proinflammatory gene response, carbonylation and lipid peroxidation injury to select brain regions, such as in one embodiment, in regions containing wake-active neurons. Collectively, the invention highlights the significance of long-term hypoxia/reoxygenation events as in sleep apnea and identify a novel pathway whereby the hypoxia/reoxygenation events induce NADPH oxidase activation in the brain, which then promotes oxidative injury, microglial activation and proinflammatory gene expression. Therefore, these findings identify a potential target pathway for prevention of neurobehavioral morbidities commonly observed in persons treated for obstructive sleep apnea (OSA).

In one embodiment, persons with OSA show evidence of oxidative stress peripherally. Isoprostane 8,12-iso-iPF2α-VI is a marker of in vivo lipid peroxidation that increases in one embodiment in long-term intermittent hypoxia (LTIH), is increased in exhaled breath condensate in patients with untreated OSA. The magnitude of isoprostane increase in persons with OSA is similar to the magnitude of increase observed in the brain in mice subjected to intermittent hypoxia. Further evidence that increased lipid peroxidation in persons with OSA relates directly to the sleep-disordered breathing is provided by the observation that effective treatment of sleep apnea with nasal CPAP results in a significant reduction in exhalate isoprostane levels. Peripheral polymorphonuclear neutrophils procured from humans with obstructive sleep apnea manifest in another embodiment, increased superoxide production in vitro relative to neutrophils from persons without OSA, and this increase in neutrophil superoxide in OSA also corrects with effective therapy for apneic events.

In one embodiment, OSA is an independent risk factor not only for neurobehavioral morbidities, but also for hypertension and ischemic heart disease, and in another embodiment, NADPH oxidase has been implicated in the pathogenesis of these disorders.

NADPH oxidase is identified in one embodiment as an important source of intermittent hypoxia-induced injury in the brain. In another embodiment, NADPH oxidase activation in persons with OSA contributes to the cardiovascular morbidities associated with this disease. The NADPH oxidase pathway is a valuable pharmacotherapeutic target for both neurobehavioral and cardiovascular morbidities of the prevalent disorder, obstructive sleep apnea.

In one embodiment, the term "treatment" refers to any process, action, application, therapy, or the like, wherein a subject, including a human being, is subjected to medical aid with the object of improving the subject's condition, directly or indirectly. In another embodiment, the term "treating" refers to reducing incidence, or alleviating symptoms, eliminating recurrence, preventing recurrence, preventing incidence, improving symptoms, improving prognosis or combination thereof in other embodiments.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. In one embodiment, method for treating a cardiovascular morbidity, a neurobehavioral morbidity or a combination thereof, resulting from Obstructive Sleep Apnea (OSA) hypopnea syndrome in a subject, may comprise in one embodiment, a method of inhibiting or reducing the incidence of neurobehavioral morbidity.

In one embodiment, the invention provides a method for treating a cardiovascular morbidity, a neurobehavioral morbidity or a combination thereof, resulting from Obstructive Sleep Apnea (OSA) hypopnea syndrome in a subject, comprising administering to said subject a therapeutically effective amount of a composition comprising an NADPH Oxidase inhibitor, wherein the NADPH Oxidase inhibitor is Apocynin, or 4-hydroxy-3'-methoxy-acetophenon, N-Vanillylnonanamide, Staurosporine, or a combination thereof in other embodiments. In another embodiment, the NADPH Oxigenase inhibitor used in the methods and compositions of the invention, is Apocynin.

In one embodiment, the methods and compositions of the invention are used to treat cardiovascular morbidities resulting from OSA, or in another embodiment, from LTIH induced hypoxia/reoxigenation. In another embodiment, the cardiovascular morbidity is hypertension, or ischemic heart disease, heart failure, stroke, baroreflex, chemoreflex, or a combination thereof in other embodiments. In another embodiment, the cardiovascular morbidity is a macrovascular morbidity such as chronic heart failure, cardiovascular death, stroke, myocardial infarction, coronary angioplasty associated restenosis, fewer coronary artery collateral blood vessels and myocardial ischemia in other embodiments.

In one embodiment, the methods and compositions of the invention are used to treat neurobehavioral morbidities resulting from OSA, or in another embodiment, from LTIH induced hypoxia/reoxigenation, wherein the neurobehavioral morbidity is depression, or sleepiness, memory impairment, Sleep Latency, maintenance of wakefulness, or a combination thereof in other embodiments.

The abnormal respiratory events associated with OSA are accompanied in one embodiment by heart rate variability and arousals from sleep, with frequent arousals being the most important factor resulting in EDS. In one embodiment, OSA results in a significant increase in light sleep stage (mainly stage 1) at the expense of deep slow wave sleep (stages 3 and 4) and REM sleep. In one embodiment, slow wave sleep is completely abolished. In one embodiment, subjects are not aware of repetitive sleep interruption (with hundreds of arousals during one night in some embodiment of OSA to be treated with the compositions and methods of the invention), but simply do not feel restored in the morning. Other nocturnal symptoms include in other embodiments, restlessness, nocturia, excessive salivation and sweating, gastroesophageal reflux, as well as headache and dry mouth or throat in the morning on awakening, or a combination thereof in other embodiment. In one embodiment, the methods and compositions of the invention are effective in treating nocturnal symptoms which are in another embodiment, neurobehavioral morbidities associated with OSA.

In one embodiment, NADPH oxidase is essential for the proinflammatory response in intermittent hypoxia modeling sleep apnea. In one embodiment, peripheral TNF-α levels are elevated in persons with untreated obstructive sleep apnea, while TNF-α levels improve with long-term CPAP therapy, supporting a direct link between proinflammatory response and OSA. The magnitude of gene expression increase resulting from LTIH is surprisingly large, similar in one embodiment, to TNF-α responses in mice subjected to severe ischemia with carotid ligation or drug-induced dopaminergic neurotoxicity in other embodiments. Local proinflammatory responses contribute in one embodiment, to neuronal injury and are an important factor in the microglial-mediated injury to neurons.

Both genetic deletion of $gp91^{phox}$, which results in a functionally inactive NADPH oxidase and pharmacological inhibition of NADPH oxidase completely prevented the COX-2, TNF-α and iNOS responses. Taken together, these findings strongly suggest that NADPH oxidase is upstream from the proinflammatory response.

In one embodiment, the invention provides methods and compositions method for treating a cardiovascular morbidity, a neurobehavioral morbidity or a combination thereof, resulting from Obstructive Sleep Apnea (OSA) hypopnea syndrome, or hypoxia/reoxigenation nuronal injury in a subject, comprising administering to said subject a therapeutically effective amount of a composition comprising an NADPH Oxidase inhibitor and a siRNA of $p67^{phox}$, having a sequence comprising SEQ ID. NOs. 2 or 3, or is substantially complimentary to SEQ ID 1, a siRNA of $p47^{phox}$, a siRNA of $gp91^{phox}$ or a combination thereof.

In one embodiment, the term "siRNA" refers to RNA interference, which in one embodiment refers to the process of sequence-specific post-transcriptional gene silencing in animals, mediated by short interfering RNAs (siRNAs). In another embodiment, the process of post-transcriptional gene silencing is an evolutionarily-conserved cellular defense mechanism used to prevent the expression of foreign genes. Such protection from foreign gene expression evolved one embodiment, in response to the production of double-stranded RNAs (dsRNAs) derived from viral infection or in another embodiment, from the random integration of transposon elements into a host genome via a cellular response that specifically destroys homologous single-stranded RNA of viral genomic RNA. In one embodiment, the presence of dsRNA in cells triggers the RNAi response.

By the term "conserved", amino acid sequences comprising the peptides of this invention remain in one embodiment, essentially unchanged throughout evolution, and exhibit homology among various species producing the protein The presence of long dsRNAs in cells stimulates in another embodiment, the activity of a ribonuclease III enzyme referred to as dicer. Dicer is involved in one embodiment, in the processing of the dsRNA into short pieces of dsRNA known as short interfering RNAs (siRNAs). Short interfering RNAs derived from dicer activity are in another embodiment about 21 to about 23 nucleotides in length and comprise about 19 base pair duplexes. Small RNAs function in one embodiment, by base-pairing to complementary RNA or DNA target sequences. When bound to RNA, small RNAs trigger RNA cleavage in another embodiment, or translational inhibition of the target sequence in another embodiment. When bound to DNA target sequences, small interfering RNAs mediate in one embodiment, DNA methylation of the target sequence. The consequence of these events, in one embodiment, is the inhibition of gene expression.

In one embodiment, the siRNA of $p67^{phox}$, or siRNA of $p47^{phox}$, siRNA of $gp91^{phox}$ or their combination in other embodiments exhibit substantial complementarity to their target sequence. In another embodiment, "complementarity" indicates that the oligonucleotide has a base sequence containing an at least 15 contiguous base region that is at least 70% complementary, or in another embodiment at least 80% complementary, or in another embodiment at least 90% complementary, or in another embodiment 100% complementary to an-at least 15 contiguous base region present of a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of $p67^{phox}$, or siRNA of $p47^{phox}$, siRNA of $gp91^{phox}$ or their combination, are sufficiently complimentary to their target sequence. "Sufficiently complementary" refers in one embodiment to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80% in one embodiment, or at least about 90% in another embodiment, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

The term "nucleic acid" refers in one embodiment to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2-O-methyl ribonucleic acids, and the like. In one embodiment, the siRNAs used in the compositions and methods of the invention, are nuscleic acid sequences.

In one embodiment, the composition of the invention described herein are used in the embodiments of the methods of the invention described herein.

In one embodiment, the invention provides a composition comprising at least two of an NADPH Oxidase inhibitor, a siRNA of $p67^{phox}$, a siRNA of $p47^{phox}$, a siRNA of $gp91^{phox}$, a COX-2 Inhibitor or a combination thereof.

Peroxides, including hydrogen peroxide ($H_2O_2$), are one of the main reactive oxygen species (ROS) leading to oxidative stress. $H_2O_2$ is continuously generated by several enzymes (including NADPH Oxidase, superoxide dismutase, glucose oxidase, and monoamine oxidase) and must be degraded to prevent oxidative damage. The cytotoxic effect of $H_2O_2$ is thought to be caused by hydroxyl radicals generated from iron-catalyzed reactions, causing subsequent damage to DNA, proteins, and membrane lipids.

In one embodiment, the invention provides methods and compositions method for treating a cardiovascular morbidity, a neurobehavioral morbidity or a combination thereof, resulting from Obstructive Sleep Apnea (OSA) hypopnea syndrome, or hypoxia/reoxigenation nuronal injury in a subject, comprising administering to said subject a therapeutically effective amount of a composition comprising an NADPH Oxidase inhibitor and a COX-2 inhibitor.

In one embodiment, COX-2 inhibitor is used in the compositions and methods of the invention. "Cyclooxygenase-2 (COX-2) inhibitor" refers in one embodiment, to a compound that selectively inhibits the cyclooxygenase-2 enzyme over the cyclooxygenase-1 enzyme. In another embodiment, the compound has a cyclooxygenase-2 $IC_{50}$ of less than about 0.5 μ·M, and also has a selectivity ratio of cyclooxygenase-2 inhibition over cyclooxygenase-1 inhibition of at least 50, or, in another embodiment of at least 100. In one embodiment, the compound has a cyclooxygenase-1 $IC_{50}$ of greater than about 1 μM, or in another embodiment, of greater than 20 μM.

Selective COX-2 inhibitors are disclosed in, for example, U.S. Pat. Nos. 5,681,842, 5,750,558, 5,756,531, 5,776,984 and in WO 98/39330, WO 99/10331 and WO 99/10332 assigned to Abbott Laboratories; and in WO 98/50075 assigned to Algos Pharmaceutical Corporation; and in U.S. Pat. No. 5,980,905 assigned to AMBI Inc.; and in U.S. Pat. Nos. 5,776,967, 5,824,699, 5,830,911 and in WO 98/04527 and WO 98/21195 assigned to American Home Products Corporation; and in WO 99/18960 assigned to Astra Pharmaceuticals Ltd.; and in U.S. Pat. No. 5,905,089 assigned to Board of Supervisors of Louisiana State University; and in WO 97/13767 assigned to Chemisch Pharmazeutische Forschungsgesellschaft MBH; and in WO 96/10021 assigned to The Du Pont Merck Pharmaceutical Company; and in WO 99/13799 assigned to Euro-Celtique; and in U.S. Pat. No. 5,134,142 and in WO 99/15505 assigned to Fujisawa Pharmaceutical Co. Ltd.; and in U.S. Pat. Nos. 5,344,991, 5,393,790, 5,521,207, 5,596,008, 5,616,601, 5,620,999, 5,633,272, 5,643,933, 5,686,470, 5,696,143, 5,700,816, 5,859,257, 5,972,986, 5,990,148 and in WO 94/15932, WO 94/27980, WO 95/15316, WO 96/16934, WO 96/25405, WO 96/38418, WO 96/38442, WO 96/41645, WO 97/38986, WO 98/06708, WO 98/43649, WO 98/47509, WO 98/47890 and WO 99/22720 assigned to G. D. Searle & Co.; and in WO 96/31509 and WO 99/12930 assigned to Glaxo Group Limited; and in WO 97/34882 assigned to Grupo Farmaceutico Almirall; and in WO 97/03953 assigned to Hafslund Nycomed Pharma AG; and in U.S. Pat. Nos. 5,945,539, 5,994,381 and in EP 0 745 596 A1 assigned to Japan Tobacco, Inc.; and in U.S. Pat. Nos. 5,686,460, 5,807,873 and in WO 97/37984 and WO 99/215.85 assigned to Laboratoires USPA; and in U.S. Pat. Nos. 5,585,504, 5,840,924, 5,883,267, 5,925,631 and in WO 97/44027, WO 97/44028, WO 97/45420, WO 98/00416, WO 98/47871, WO 99/15503, WO 99/15513, WO 99/20110, WO 99/45913 and WO 99/55830 assigned to Merck & Co. Inc.; and in U.S. Pat. Nos. 5,409,944, 5,436,265, 5,474,995, 5,536,752, 5,550,142, 5,510,368, 5,521,213, 5,552,422, 5,604,253, 5,604,260, 5,639,780, 5,677,318, 5,691,374, 5,698,584, 5,710,140, 5,733,909, 5,789,413, 5,817,700, 5,840,746, 5,849,943, 5,861,419, 5,994,379 and in EP 0 788 476 B1, EP 0 863 134 A1 and in WO 94/20480, WO 94/13635, WO 94/26731, WO 95/00501, WO 96/19469, WO 96/37467, WO 97/14691, WO 97/16435, WO 97/28120, WO 97/28121, WO 97/36863, WO 98/03484, WO 98/43966, WO 99/14194, WO 99/14195 and WO 99/23087 assigned to Merck Frosst Canada & Co., and in WO 99/59635 assigned to Merck Sharp & Dohme Limited; and in U.S. Pat. No. 5,380,738 assigned to Monsanto Company; and in WO 99/33796 assigned to Nissin Food Products Co. Ltd.; and in U.S. Pat. No. 5,783,597 assigned to Ortho Pharmaceutical Corporation; and in WO 98/07714 assigned to Oxis International Inc.; and in EP 0 937 722 A1 and in WO 98/50033 and WO 99/05104 assigned to Pfizer Inc.; and in U.S. Pat. No. 5,908,858 assigned to Sankyo Company Limited; and in WO 97/25045 assigned to Smithkline Beecham Corporation; and in U.S. Pat. No. 5,475,021 assigned to Vanderbilt University; and in WO 99/59634 assigned to Wakamoto Pharmaceutical Co. Ltd., the disclosures of each of which are incorporated by reference herein in their entirety.

The activity of the selective COX-2 inhibitors of the present invention may be demonstrated by the following assays. COX-1 activity is determined by methods well known to those skilled in the art. The human cell based COX-2 assay is carried out as previously described (Moore et al., Inflam. Res., 45, 54, 1996). The in vivo Carrageenan induced foot edema rat study is carried out as previously described in Winter et al., Proc. Soc. Exp. Biol. Med., 111, 544, 1962. IN one embodiment, COX-2 selectivity can be determined by methods well known to those skilled in the art and particularly by ratio in terms of $IC_{50}$ value of COX-1 inhibition to COX-2 inhibition. In one embodiment, a compound showing a COX- 1/COX-2 inhibition ratio of more than 2 has good COX-2 selectivity and may be used in the compositions and methods of the invention.

In another embodiment, contacting the sample with the compositions of the invention, comprises amplifying the target gene encoding for NADPH Oxigenase. In one embodiment, the term "amplification" or "amplify" refers to one or more methods known in the art for copying a target nucleic acid, thereby increasing the number of copies of a selected nucleic acid sequence. Amplification may be exponential in one embodiment, or linear in another. In one embodiment, a target nucleic acid may be either DNA or RNA. The sequences amplified in this manner form an "amplicon." While the exemplary embodiments described herein relate to amplification using the polymerase chain reaction ("PCR"), numerous other methods are known in the art for amplification of nucleic acids (e.g., isothermal methods, rolling circle methods, etc.) and are considered within the scope of the present invention. The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860.

In another embodiment, real time PCR is used in the methods of the invention. The term "real time PCR" refers in one embodiment to the process where a signal emitted from the PCR assay is monitored during the reaction as an indicator of amplicon production during each PCR amplification cycle (i.e., in "real time"), as opposed to conventional PCR methods, in which an assay signal is detected at the endpoint of the PCR reaction. Real time PCR is based in one embodiment on the detection and quantitation of a fluorescent reporter. The signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. For a general description of "real time PCR" see Dehe et al. J. Virol. Meth. 102:37-51 (2002); and Aldea et al. J. Clin. Microbiol. 40:1060-1062 (2002) (referring to the "LightCycler," where real-time, kinetic quantification allows measurements to be made during the log-linear phase of a PCR).

In one embodiment, the methods and compositions of the invention are use to treat a subject, wherein the subject is a snorer or at risk for developing sleep disordered breathing. Sleep-disordered breathing, which in one embodiment includes apneas, hypopneas and respiratory effort related arousals (RERAs), is the hallmark of OSA. The severity of sleep-disordered breathing is assessed in one embodiment, by combining the number of apneas and hypopneas per hour of sleep in an index called the apnea-hypopnea index (AHI) or the respiratory disturbance index (RDI). This index has been shown to be both a reproducible measurement and a predictor of associated cardiovascular disease. The severity of oxygen desaturation and sleep fragmentation during polysomnography are combined in one embodiment with clinical symptoms to assess the immediate consequences to the individual from the sleep-disordered breathing.

In one embodiment, the sleep disordered breathing which the subject is at risk of developing and for which the subject may be treated by the methods and compositions of the invention is Apnea, which is characterized by a cessation of airflow for 10 seconds or more. In one embodiment, the sleep disordered breathing which the subject is at risk of developing and for which the subject may be treated by the methods and compositions of the invention is Hyponea, which refers in one embodiment to the reduction without cessation in airflow or effort. In another embodiment, Hypopnea refers to the degree of airflow or respiratory effort reduction, inclusion and degree of oxygen desaturation, and inclusion of arousal from sleep. In one embodiment, the sleep disordered breathing which the subject is at risk of developing and for which the subject may be treated by the methods and compositions of the invention is RERAs, which refers in another embodiment to a reduction of airflow culminating in EEG arousal but not meeting criteria for apnea or hypopnea.

In one embodiment, the compositions of the invention described herein are used in the embodiments of the methods of the invention.

In one embodiment, administration of the compositions used in the methods of the invention takes place sequentially in separate formulations, or is accomplished by simultaneous administration in a single formulation or separate formulations in other embodiments. Administration is accomplished in one embodiment, by oral route, or by intravenous, intramuscular or subcutaneous injections in other embodiment. The formulation may be in the form of a bolus, or in the form of aqueous or non-aqueous isotonic sterile injection solutions or suspensions. These solutions and suspensions may be prepared from sterile powders or granules having one or more pharmaceutically-acceptable carriers or diluents, or a binder such as gelatin or hydroxypropyl-methyl cellulose, together with one or more of a lubricant, preservative, surface-active or dispersing agent.

In one embodiment, the composition further comprises a carrier, excipient, lubricant, flow aid, processing aid or diluent, wherein said carrier, excipient, lubricant, flow aid, processing aid or diluent is a gum, starch, a sugar, a cellulosic material, an acrylate, calcium carbonate, magnesium oxide, talc, lactose monohydrate, magnesium stearate, colloidal silicone dioxide or mixtures thereof.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetner, a film forming agent, or any combination thereof.

In one embodiment, the composition is a particulate composition coated with a polymer (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, or intracranially.

In one embodiment, the compositions of this invention may be in the form of a pellet, a tablet, a capsule, a solution, a suspension, a dispersion, an emulsion, an elixir, a gel, an ointment, a cream, or a suppository.

In another embodiment, the composition is in a form suitable for oral, intravenous, intraaorterial, intramuscular, subcutaneous, parenteral, transmucosal, transdermal, or topical administration. In one embodiment the composition is a controlled release composition. In another embodiment, the composition is an immediate release composition. In one embodiment, the composition is a liquid dosage form. In another embodiment, the composition is a solid dosage form.

The compounds utilized in the methods and compositions of the present invention may be present in the form of free bases in one embodiment or pharmaceutically acceptable acid addition salts thereof in another embodiment. In one embodiment, the term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I are prepared in another embodiment, from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, b-hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, in another embodiment, the appropriate acid or base with the compound.

In one embodiment, the term "pharmaceutically acceptable carriers" includes, but is not limited to, may refer to 0.01-0.1M and preferably 0.05M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

In one embodiment, the compounds of this invention may include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The pharmaceutical preparations of the invention can be prepared by known dissolving, mixing, granulating, or tablet-forming processes. For oral administration, the active ingredients, or their physiologically tolerated derivatives in another embodiment, such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the active ingredients or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The active agent is administered in another embodiment, in a therapeutically effective amount. The actual amount administered, and the rate and time-course of administration, will depend in one embodiment, on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences.*

Alternatively, targeting therapies may be used in another embodiment, to deliver the active agent more specifically to certain types of cell, by the use of targeting systems such as antibodies or cell specific ligands. Targeting may be desirable in one embodiment, for a variety of reasons, e.g. if the agent is unacceptably toxic, or if it would otherwise require too high a dosage, or if it would not otherwise be able to enter the target cells. In one embodiment, the compositions of the invention further provide a ligand for nuronal cells, such as, in one embodiment CD11.

The compositions of the present invention are formulated in one embodiment for oral delivery, wherein the active compounds may be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound sucrose as a sweetening agent methyl and propylparabens as preservatives, a dye and flavoring, such as cherry or orange flavor. In addition, the active compounds may be incorporated into sustained-release, pulsed release, controlled release or postponed release preparations and formulations.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, the composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Such compositions are in one embodiment liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms, protective coatings, protease inhibitors, or permeation enhancers for various routes of administration, including parenteral, pulmonary, nasal, and oral.

In another embodiment, the compositions of this invention comprise one or more, pharmaceutically acceptable carrier materials.

In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

The dosage regimen for treating a condition with the compositions of this invention is selected in one embodiment, in accordance with a variety of factors, such as the type, age, weight, ethnicity, sex and medical condition of the subject, the severity of the condition treated, the route of administration, and the particular compound employed, and thus may vary widely while still be in the scope of the invention.

In one embodiment, the invention provides a method of treating brain oxidative injury, microglial activation or proinflammatory gene expression, induced by long-term intermittent hypoxia (LTIH) in a region of the brain, comprising contacting said region with a composition comprising NADPH Oxigenase inhibitor.

In one embodiment, the term "contacting a region", refers to any exposure of a region to a peptide, nucleic acid, or compositions of this invention. Regions may be in direct contact with compounds- and compositions of the invention, or exposed indirectly, through methods well described in the art. For example the magnocellular preoptic region, wherein the media is supplemented with any of the siRNAs of $p67^{phox}$, $p47^{phox}$, $gp91^{phox}$, COX-2 inhibitor compounds or compositions would be an example of a method of contacting a region, considered a part of this invention. Another example would be oral or parenteral administration of siRNAs of $p67^{phox}$, $p47^{phox}$, $gp91^{phox}$, COX-2 composition, whose administration results in vivo regional exposure to these compounds, within specific sites within a brain. Such administration is also considered as part of this invention, as part of what is meant by the phrase "contacting a region".

In one embodiment, the compositions of the invention are used in treating brain oxidative injury, microglial activation or proinflammatory gene expression, induced by long-term intermittent hypoxia (LTIH) in a region of the brain. In one embodiment, the region of the brain being treated for oxidative injury, microglial activation or proinflammatory gene expression, induced by long-term intermittent hypoxia (LTIH) is the magnocellular preoptic region, or substantia inominata, the lateral hypothalamus in the region of the orexinergic neurons, the histaminergic wake-active neurons or a combination thereof in other embodiments.

In one embodiment, NADPH oxidase is essential for the proinflammatory response in intermittent hypoxia modeling sleep apnea. In another embodiment. peripheral TNF-α levels are elevated in persons with untreated obstructive sleep apnea, while TNF-α levels improve with long-term CPAP therapy, supporting a direct link between proinflammatory response and OSA. The magnitude of gene expression increase observed in one embodiment, is surprisingly large, similar to TNF-α responses in mice subjected to severe ischemia with carotid ligation or drug-induced dopaminergic neurotoxicity. Local proinflammatory responses contribute in one embodiment to neuronal injury and are an important factor in the microglial-mediated injury to neurons in another embodiment. In one embodiment, genetic deletion of $gp91^{phox}$, results in a functionally inactive NADPH oxidase or in another embodiment, pharmacological inhibition of NADPH oxidase completely, prevents the COX-2, TNF-α and iNOS proinflammatory responses. in one embodiment, NADPH oxidase is upstream from the proinflammatory response and modulating its activity with the methods and compositions of the invention will prevent this response.

Long-term intermittent hypoxia due to respiratory pauses in subjects with obstructive sleep apnea (OSA) is closely accompanied in one embodiment by recurrent increases in sympathetic activity, blood pressure (BP), and heart rate (HR) during sleep, with the repeated hemodynamic activation being used to explain the increased nocturnal release of natriuretic peptides into the circulation, a foremost hormonal characteristic of OSA.

Figure 2:
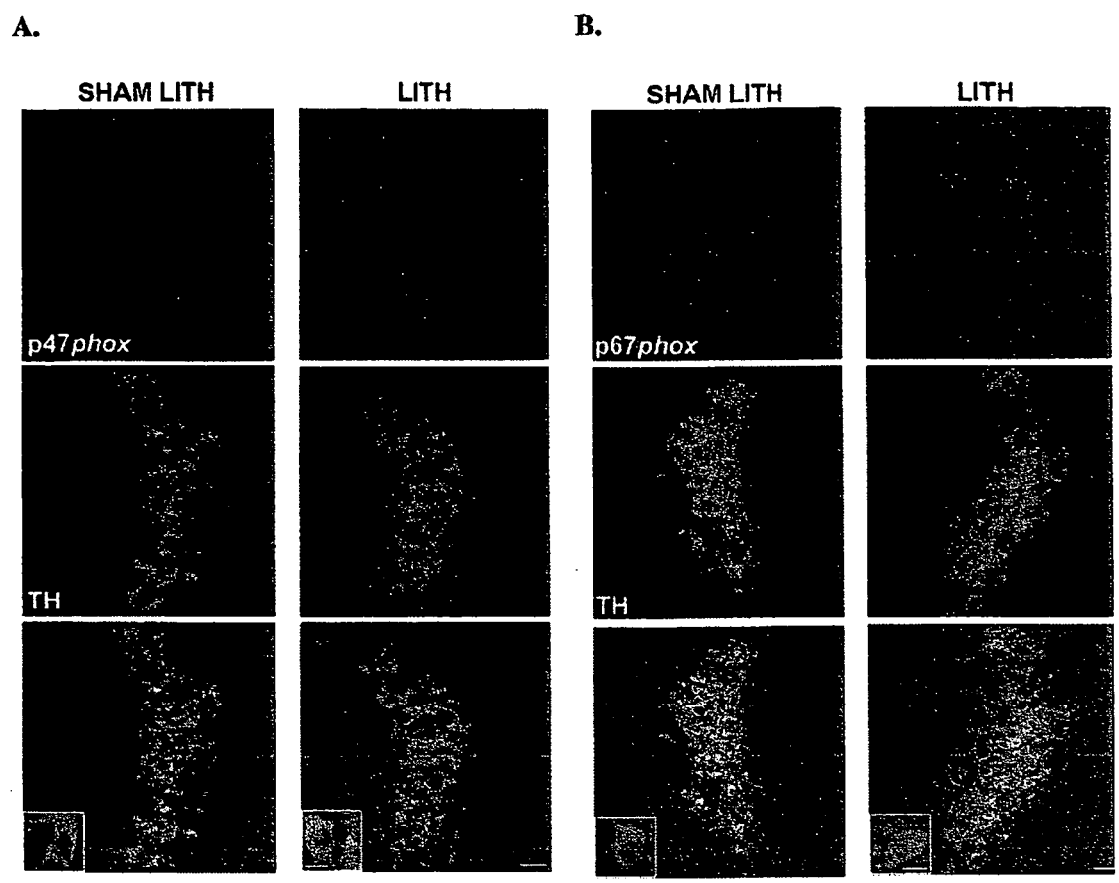
FIG. 2 A.) Immunohistochemical staining of noradrenergic locus coeruleus wake-active region shows enhanced NADPH oxidase subunit $p67^{phox}$ and $p47^{phox}$ expression in locus coeruleus in mice exposed to LTIH. B) Double labeling with tyrosine hydroxylase localizes both subunits $p67^{phox}$ and $p47^{phox}$ to noradrenergic locus coeruleus wake-active neurons. Lower panel scale bar is 50 µm and inlay bar is 20 µm.

In one embodiment, an increased $p67^{phox}$ and $p47^{phox}$ immunoreactivity is found in the noradrenergic locus coeruleus neurons (FIG. 2A). In another embodiment, LTIH results in increased NADPH oxidase subunit gene and protein expression in wake-active regions of the brain, or in another embodiment, within the locus coeruleus, the increase is evident within noradrenergic neurons.

In one embodiment, treating the brain oxidative injury, microglial activation or proinflammatory gene expression, induced by long-term intermittent hypoxia (LTIH) in a region of the brain, comprises inhibiting or preventing said injury or reducing the severity of the injury in another embodiment.

In one embodiment, the cells used for the methods of the invention are obtained from a sample given by the subject. The sample to be analyzed may consist in one embodiment of, or comprise blood, sera, urine, mucosa, feces, epidermal sample, skin sample, cheek swab, sperm, amniotic fluid, cultured cells, bone marrow sample or chorionic villi, and the like. A biological sample may be processed in another embodiment to release or otherwise make available a nucleic acid or a protein for detection as described herein. Such processing may include in one embodiment steps of nucleic acid manipulation, e.g., preparing a cDNA by reverse transcription of RNA from the biological sample. Thus, the nucleic acid to be amplified in one embodiment by the methods of the invention may be DNA or RNA.

As used herein, "subject" refers in one embodiment, to a human or any other animal which contains a NADPH Oxigenase that can be detected. A subject can be a patient, which refers to a human presenting to a medical provider for diagnosis or treatment of a disease. A human includes pre and post natal forms. In one embodiment, subjects are humans being treated for a brain oxidative injury, a microglial activation or a proinflammatory gene expression, induced by long-term intermittent hypoxia (LTIH).

The term "about" as used herein means in quantitative terms plus or minus 5%, or in another embodiment plus or minus 10%, or in another embodiment plus or minus 15%, or in another embodiment plus or minus 20%.

In one embodiment, the invention provides a method for predicting the probability of developing hypoxia/reoxygenation proinflammatory nuronal injury in a subject, comprising obtaining a nuronal cell from a subject; and analyzing said nuronal cell for the presence of NADPH Oxigenase wherein presence of NADPH Oxidase indicates vulnerability to hypoxia/reoxygenation proinflammatory nuronal injury.

The following examples are presented in order to more fully illustrate the preferred embodiments of the invention. They should in no way be construed, however, as limiting the broad scope of the invention.

EXAMPLES

Materials and Methods

Animals

Ten-week old male C57BL/6J (B6) mice, $gp91^{phox}-/-$ mice (B6.129S6-Cybb$^{tm1din}$) backcrossed 12 generations to C57BL/6J 000664 and $gp91^{phox}+/+$ (WT) backcrossed substrain C57BL/6J 000664 mice (Jackson Laboratory, Bar Harbor, Me.) were studied. Methods and study protocols were approved in full by the Institutional Animal Care and Use Committee of the University of Pennsylvania, conforming with the revised NIH Office of Laboratory Animal Welfare Policy. Food and water were provided ad libitum. Mice were confirmed pathogen free at the time of studies.

Long-Term Intermittent Hypoxia Protocol

A detailed description of the long-term intermittent hypoxia (LTIH) protocol was recently published. An automated nitrogen/oxygen delivery profile system (Oxycycler model A84XOV; Biospherix, Redfield, N.Y.) produced brief reductions in housing chamber ambient oxygen levels from 21% to 10% for 5 sec every 90 sec, resulting in arterial oxyhemoglobin saturation fluctuations between 95-98% and 83-86%. Sham LTIH, with ambient $FIO_2$ fluctuations from 21% to 19% every 90 sec, held arterial oxyhemoglobin values constant between 96-98%. Both conditions were produced for 10 hr of the lights-on period for a total of 8 wks. Humidity, ambient $CO_2$ and environmental temperature were held constant.

Measurement of Regional $p67^{phox}$, Microglial and Proinflammatory Gene Responses to LTIH To determine if LTIH results in lasting increases in NADPH oxidase and microglial gene responses, real-time Taqman PCR was performed on laser-captured microdissections or macropunches of selected brain regions in mice exposed to sham LTIH or LTIH, two weeks into recovery to parallel sleep studies, using our methods, as previously published (12, 25). Real-time measurement of a NADPH oxidase subunit ($p67^{phox}$). To accomplish this, two weeks following conditions of either sham LTIH or LTIH, mice were perfused with PBS; brains were immediately frozen and sectioned (10 µm) for laser-capture microdissections of the following wake-active or hypoxia sensitive regions: frontal cortex (layer V), nucleus basalis Meynert/substantia inominata/horizontal diagonal band, hippocampus CA1, striatum, lateral hypothalamus, dorsal raphe nucleus, and locus coeruleus, or the following sleep-active adjacent brain regions: median septal diagonal band, medial preoptic area, and ventrolateral preoptic area, collecting 100 captures (40 μm diameter) per region in each mouse (n=6 mice/condition). RNA was purified and cDNA created for primer sets for primer/probe sets in Table 1, for Taqman real time PCR (SDS-7900HT, ABI). All primer probe sets showed excellent sensitivity and linearity (detection of ≥100 copies/sample, $r^2 \geq 0.99$).

A second series of mice used for LTIH gene responses were $gp91^{phox}$–/– and +/+ mice exposed to either sham LTIH or LTIH for proinflammatory responses. To run real-time for four genes on the same sample, we used macrodissections (1 mm³ punches) of selected brain regions (n=6 to 12 mice/strain/LTIH condition), from the following areas: frontal cortex, lateral basal forebrain, CA1 hippocampus, lateral hypothalamus and medial septum, using the primer/probe sets for $p67^{phox}$, COX-2, TNF-a, iNOS, listed in Table 1.

cryoprotectant at –20° C. Before immunohistochemical processing, brain sections were thoroughly washed in buffer to remove cryoprotectant. Sections were incubated with antibodies against NADPH oxidase components ($p67^{phox}$ and $p47^{phox}$, 1:50, Upstate) and tyrosine hydroxylase (1:1000 dilution, Chemicon) for 48 hrs at 4° C. Tissue sections were then incubated with secondary antibodies (Alexa 488 and Alexa 594, 1:200, Molecular Probes) for 2 hrs at room temperature. The tissues were subsequently washed in several changes of PBS, mounted on gelatin coated slides, dehydrated in increasing concentrations of ethanol, cleared in xylene and coverslipped with Cytoseal 60 (VWR Scientific). Analysis was preformed using a Zeiss LSM 510 Meta confocal microscope system.

Protein Carbonyl ELISA

Concentrations of protein carbonyls in macrodissections of the lateral basal forebrain, in mice exposed to LTIH or sham

TABLE 1

Primer and probe gene identification and sequences

| Gene | Genbank | Sequences |
|---|---|---|
| $P67^{phox}$ | AB002664 | Sense=CGCTCTCGCCAGAACACA, (1244-1261, SEQ ID NO. 1)<br>Antisense=TTGGTCACCCACCGTATGCT; (1392-1373, SEQ ID NO. 2)<br>Probe=CTACCGGCGTCGGGACAGCC (1272-1291, SEQ ID NO. 3) |
| TNF-α | NM_013693 | Sense=CCAGGTTCTCTTCAAGGGACAA; (573-594, SEQ ID NO. 4)<br>Antisense=CGGCAGAGAGGAGGTTGACTT; (679-659, SEQ ID NO. 5)<br>probe=CCTCACCCACACCGTCAGCCG (615-635, SEQ ID NO. 6) |
| iNOS | NM_010927 | Sense=CAGGAGATGGTCCGCAAGAG; (3254-3273, SEQ ID NO. 7)<br>Antisense=AATTTCTGCAGCCATTTCCTTCT; (1509-1530, SEQ ID NO. 8)<br>Probe=TGCACACAGGCTACTCCCGGC (3288-3308, SEQ ID NO. 9) |
| COX-2 | NM_011434 | Sense=TCCATTGACCAGAGCAGAGAGA; (1409-1430, SEQ ID NO. 10)<br>Antisense=AATTTCTGCAGCCATTTCCTTCT; (1509-1530, SEQ ID NO. 11)<br>Probe=TTCTCCCTGAAGCCGTACACATCA (1409-1430, SEQ ID NO. 12) |

To determine if NADPH oxidase inhibition would also prevent LTIH gene responses, a third series of mice examined for gene responses were WT mice treated systemically throughout LTIH or sham LTIH with 3 mg/kg/day apocynin (Sigma-Aldrich) in DMSO, DMSO or PBS delivered subcutaneously (n=10/group) by way of micro-osmotic pump (1002, Durect, Cupertino, Calif.). Apocynin was selected over diphenylene iodinium, as the latter also inhibits nitric oxide synthases, xanthine oxidase and other flavoenzymes, and DMSO vehicle groups were included in the study and compared to saline pumps, as this hydrophobic diluent has hydroxyl scavenging activity and thus, some neuroprotective effect in ischemic reperfusion studies.

Immunoreactivity to $p47^{phox}$ and $p67^{phox}$ in Wake-Active Regions

Cytosolic and membrane/organelle fractions in WT mice exposed to LTIH or sham LTIH but not allowed normoxia recovery (n=5 per condition) were separated using 100,000 G×60 min (19, 20). Polyclonal rabbit anti-mouse $p47^{phox}$ and $p67^{phox}$ (1:500, Upstate) added to homogenates was bound by a horseradish peroxidase conjugated secondary anti-IgG (1:15,000, 12-349, Upstate) and detected with chemiluminescence (SuperSignal Ultra, Pierce). Images were analyzed with NIH Image Analysis. Preliminary trials showed weak immunoreactivity 2 weeks into recovery.

Immunohistochemical Analysis

Mice were anesthetized and perfused transcardially with buffered aldehyde solution to preserve antigenicity of target proteins. Brains were post-fixed and sectioned at 20 μm in a coronal plane with a freezing microtome prior to storage in LTIH and then allowed two week normoxic recovery, were determined using a commercially available ELISA kit (Zentec PC Test, Zenith Technology, Dunedin, New Zealand), developed from established techniques (29), modified as recently described.

Measurement of $F_2$ Isoprostanes

Isoprostane, $d_4$-8,12-iso-iPF$_{2\alpha}$-VI, ($F_2$-iPs) analysis was performed as previously described also two weeks into recovery (8, 12, 30) using macrodissections (0.5 mm³ bilaterally) from the lateral basal forebrain in mice following conditions of LTIH and Sham IH mice for both $gp91^{phox}$–/– and +/+ strains. Thin layer chromatography was used for purification of the eluate, and negative ion chemical ionization gas chromatography-mass spectrometry was used to assay $F_2$-iPs.

Sleep/Wake Protocol and Analysis of Sleepiness

After 8 wks of LTIH or sham LTIH exposures, mice were returned to normoxic conditions for 1 wk. Surgical implantation of electrodes and electrophysiological recordings followed using previously described electrode implantation methods (32). Following 3 d post-operative recovery, mice were connected to recording cables in individual cages, and 4 d later sleep recordings were initiated (beginning 2 wk into recovery from LTIH). Baseline sleep was recorded for 5 days. On recording day 6, a baseline murine multiple sleep latency test (MMSLT) was performed (4 nap opportunities between 2 p.m. and 4 p.m.) to measure baseline sleep propensity (33). On recording day 7, sleep deprivation was performed for 6 hours of the light period (8 a.m. to 2 p.m.), followed by a second MSLT and then recovery sleep was recorded for 12 h. The behavioral state acquisition and analysis program used for these studies was ACQ 3.4 (34), with modifications and behavioral state parameters as previously described (7, 9, 32). Primary variables were total sleep time/24 hr, total NREM sleep time/24 hr and REM sleep time/24 hr, and average sleep latency, before and after short-term sleep loss.

Statistical Analysis

Values reported represent mean±SEM. Parameter differences were analyzed with one and two-way ANOVA, with LTIH conditions, brain region, strain or drug treatment as the independent variables. When significant overall differences were observed, a priori within group comparisons of means were made using Bonferroni t post-tests for pre-selected groups. The null hypothesis was rejected for probabilities <0.05.

Example 1

Long-Term Hypoxia/Reoxygenation Increases NADPH Oxidase Gene Expression and Results in Increased NADPH Oxidase in Wake-Active Neurons To determine whether long-term intermittent hypoxia (LTIH) increases NADPH oxidase gene expression in wake-active brain regions, NADPH oxidase gene response was measured in discrete brain regions by performing laser-captured microdissections in adult WT mice (n=10 sham LTIH; n=10 LTIH) for Taqman real-time PCR measurement of mRNA copies. LTIH increased NADPH oxidase subunit p67$^{phox}$ gene expression in most, but not all wake-active regions: the lateral basal forebrain (p<0.001), the dorsal raphe nucleus (p<0.001), and the locus coeruleus (p<0.05), but not significantly in the lateral hypothalamus (N.S.), as illustrated in FIG. 1A. To determine whether NADPH oxidase subunit proteins were increased in response to LTIH, Western blots were performed on homogenates from two representative wake-active regions, the locus coeruleus and the lateral basal forebrain. Micropunches from WT mice after sham LTIH and LTIH revealed increased p47$^{phox}$ in both regions in WT mice exposed to LTIH (FIG. 1B). p47$^{phox}$ protein as measured by relative density at the 47 KD band increased by 50%, t=2.9, p<0.05 in the lateral basal forebrain and by 65% in the locus coeruleus, t=2.8, p<0.05. To determine whether NADPH oxidase protein was qualitatively increased within representative wake-active neurons, immunohistochemistry for two of the NADPH oxidase subunits was performed in WT mice exposed to 8 wks LTIH or sham LTIH for the noradrenergic locus coeruleus. An increased p67$^{phox}$ and p47$^{phox}$ immunoreactivity was found in the noradrenergic locus coeruleus neurons (FIG. 2A). Thus, LTIH results in increased NADPH oxidase subunit gene and protein expression in wake-active regions of the brain, and within the locus coeruleus, the increase is evident within noradrenergic neurons.

Example 2

Genetic Deletion of NADPH Oxidase Subunit gp91$^{phox}$ Confers Resistance to Long-Term Hypoxia Reoxygenation-Induced Hypersomnolence and Sleepiness To establish a critical role for NADPH oxidase in long-term intermittent hypoxia (LTIH) hypersomnolence and sleepiness, a series of gp91$^{phox}$ null and gp91$^{phox}$ wild type (WT) mice were exposed to 8 wks of LTIH or sham LTIH (n=10-12 for each strain/condition) and were then implanted with electroencephalographic and electromyographic electrodes for sleep recordings to compare effect of LTIH on sleep and wakefulness across genotype two weeks after LTIH and sham LTIH were completed.

The effect of LTIH on wake and sleep times/24 hr period varied with genotype, F=17.3, p<0.01. WT mice exposed to LTIH had a large reduction in wake time/24 hr, relative to sham exposed WT mice (−200 min wake/24 hr, t=4.1, p<0.001), a large increase in NREM sleep time, (174 min/24 hr, t=3.5, p<0.01 and a trend towards increased REM sleep time, t=2.1, p=0.05, FIG. 2A). In contrast, sleep and wake times in gp91$^{phox}$ null mice were not affected by LTIH; there were no difference across gp91$^{phox}$ null mice across LTIH and sham LTIH for wake time, F=0.7 or NREM sleep times, F=6, as detailed in FIG. 3A. Therefore, genetic deletion of the gp91$^{phox}$ subunit of NADPH oxidase confers resistance to LTIH-induced reductions in wakefulness.

The LTIH effect on sleep latency also varied with genotype, F=18, p<0.0001 (FIG. 2B). Baseline sleep latency was reduced in WT mice exposed to LTIH (t=2.9, p<0.05) and markedly reduced relative to sham LTIH mice (t=4.8, p<0.0001), while no effect of LTIH (LTIH vs. sham LTIH) was observed in gp91$^{phox}$ null mice. Sleep latency in gp91$^{phox}$ null mice exposed to LTIH, however, was reduced by short-term (6 hr) enforced wakefulness in both the sham LTIH and LTIH (t's=4.8 and 5.1, respectively, both p<0.0001), suggesting that the homeostatic regulation is intact in the mutant mice. In summary genetic deletion of gp91$^{phox}$ prevents LTIH-induced sleepiness without impairing sleep loss sleepiness.

Example 3

Gp91$^{Phox}$ Null Mice are Resistant to LTIH-Induced Oxidative Protein Damage

Figure 4:
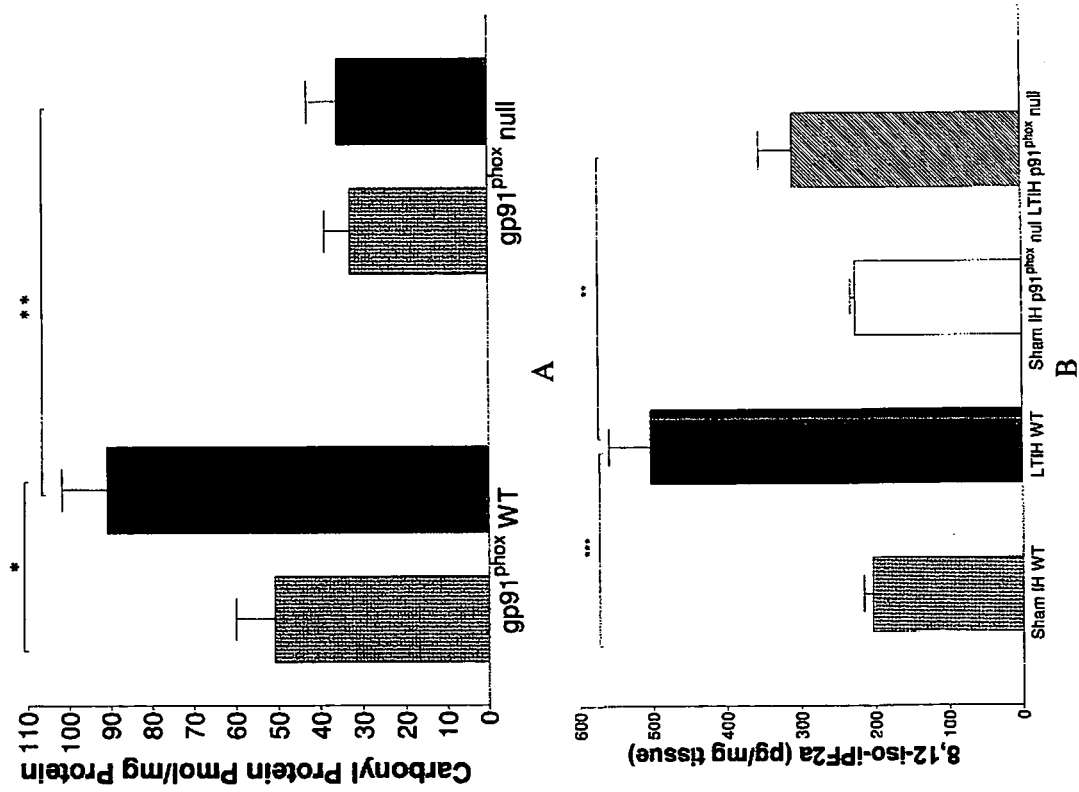
FIG. 4. NADPH oxidase is essential for basal forebrain carbonyl and isoprostane responses to long-term intermittent hypoxia. A. Carbonyl content as measured with ELISA in lateral basal forebrain macropunches in $gp91^{phox}$ null mice and wild type controls following 8 wks LTIH (black bar) or sham LTIH exposures (gray bars). Carbonyl content (carbonyl protein/20 mg protein aliquot) is significantly increased in wild type ($gp91^{phox}$+/+) mice exposed to LTIH (n=10), relative to sham LTIH exposure (n=11), * $p<0.05$. In contrast, $gp91^{phox}$ null mice showed no effect of LTIH on carbonyl content, N.S. , $p<0.01$, LTIH $gp91^{phox}$+/+ vs. LTIH $gp91^{phox}$–/–. B. Homogenized tissue samples were collected for measurement of isoprostane, 8,12-iso-iPF2-VI, from the lateral basal forebrain in mice following 8 wks exposure to either LTIH or sham LTIH. Using an internal standard, levels were assayed by negative ion chemical ionization gas chromatography and mass spectrometry. *, $p<0.001$, wild type sham LTIH vs. wild type LTIH. *, $p<0.05$, wild type LTIH vs. $gp91^{phox}$ null LTIH.

Macrodissections of the lateral basal forebrain and the noradrenergic locus coeruleus were obtained from gp91$^{phox}$ null and WT mice exposed to LTIH or sham LTIH (n=10-11/ strain and condition). The carbonyl content in the lateral basal forebrain in gp91$^{phox}$ null mice relative to WT mice for sham LTIH appeared reduced by approximately 40%; however, this did not reach statistical significance (t=2.9, p=0.05, FIG. 4A). WT mice exhibited an increase in carbonyl content in response to LTIH, relative to sham LTIH, t=3.9, p<0.05. In contrast, gp91$^{phox}$ null mice did not show an increase in response to LTIH, N.S. Similar changes were observed in the locus coeruleus region. Thus, genetic deletion of gp91$^{phox}$ prevents the LTIH carbonyl response in representative brain regions contributing to wakefulness control.

Isoprostane levels were measured in similarly dissected lateral basal forebrain tissue blocks from mice (n=5/IH condition and genotype). Gp91$^{phox}$ null mice exposed to LTIH, relative to WT mice exposed to LTIH, had reduced isoprostanes in both the lateral basal forebrain and lateral hypothalamus, (p<0.01 for both regions); however, a trend towards increased isoprostanes in the LTIH-exposed gp91$^{phox}$ null mice relative to sham LTIH gp9 phox null mice, 25%, p=0.06, suggests that the lipid peroxidation may not be completely blocked, FIG. 4B).

Example 4

Figure 3:
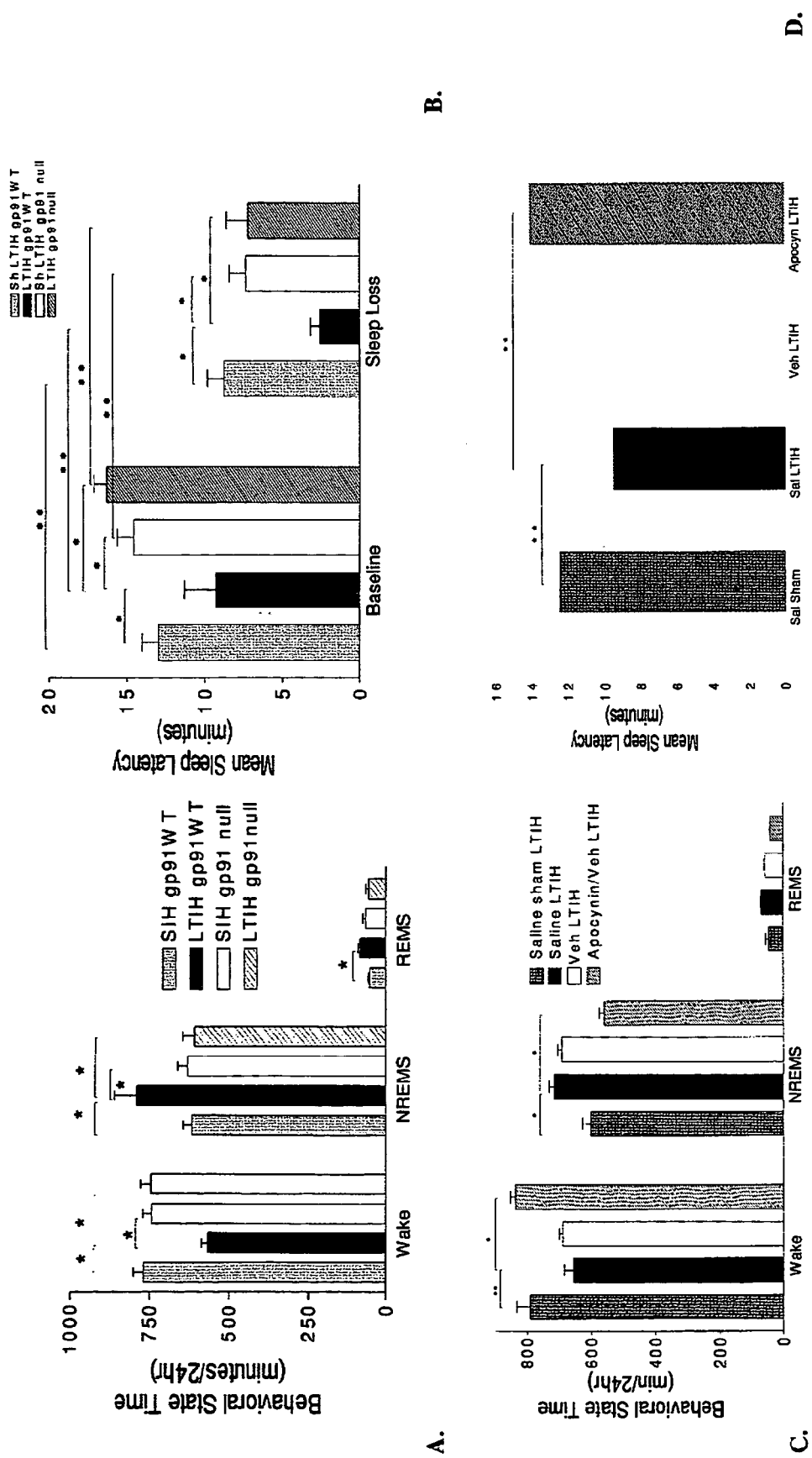
FIG. 3. NADPH oxidase is essential for the residual wake impairments following long-term intermittent hypoxia (LTIH). A. Wild type control mice exposed to LTIH (LTIH gp91WT) show reduced wake time/24 hrs and increased non-rapid-eye movement sleep (NREMS) at 2 wks into normoxic recovery relative to sham LTIH (SIH WT). In contrast, mice lacking NADPH oxidase subunit $gp91^{phox}$ exposed to LTIH (LTIH $gp91^{phox}$ null) show no effect of LTIH on either wakefulness or NREMS. B. The propensity to fall asleep, measured as the average sleep latency across four nap opportunities at the end of the lights on period, is markedly reduced in WT mice exposed to LTIH (for both unperturbed baseline sleep and after 6 hrs sleep loss, $p<0.0001$. In contrast, no effect of LTIH is observed for sleep latencies in $gp91^{phox}$ null mice, despite a marked sleep loss effect on latencies for both sham LTIH and LTIH gp91 null mice, $p<0.0001$. Shown are sleep latencies after unperturbed rest activity (Baseline) and after 6 hrs of enforced wakefulness, same circadian time point (Sleep Loss). C, Systemic apocynin treatment via osmotic pump (diagonal stripe column) prevented LTIH-induced impaired wakefulness and hypersomnolence in WT mice. In contrast, the apocynin vehicle (veh), dimethylsulfoxide was without effect (white bars). D. Apocynin therapy prevented LTIH reduced sleep latency. Values presented are means±SEM; asterisks denote statistical significance. Asterisk for all panels: *, $p<0.05$; **$p<0.001$.

Inhibition of NADPH Oxidase Throughout LTIH Exposure Prevents Hypersomnolence and Sleepiness To further investigate the role of NADPH oxidase in the LTIH-induced hypersomnolence and sleepiness, a series of WT mice were implanted with osmotic pumps to systemically deliver either a selective NADPH oxidase inhibitor, apocynin at 3 mg/kg/day, vehicle (dimethylsulfoxide, DMSO) or buffered saline throughout LTIH exposure for 8 wks. Pumps were removed and mice were implanted for sleep recordings as described above for studies in gp91$^{phox}$ null mice. Apocynin therapy prevented both LTIH reduced wake times and shortened sleep latency. WT mice treated throughout LTIH with apocynin, relative to saline treatment (t=4.5, p<0.001) and relative to DMSO vehicle (t=2.9, p<0.05) had increased wake times, and reduced NREMS time (t=4.1, p<0.001; t=2.7, p<0.05, respectively as shown in FIG. 3C). In addition to completely preventing LTIH reduced wake times for 24 hr, systemic delivery of apocynin also prevented LTIH reduced sleep latencies. Specifically, sleep latencies in apocynin treated mice were significantly higher than LTIH DMSO vehicle-treated mice, t=3.4, p<0.01, and were not significantly different from sleep latencies in WT mice without any intervention or following sham LTIH treatment (FIG. 3D).

Example 5

Figure 5:
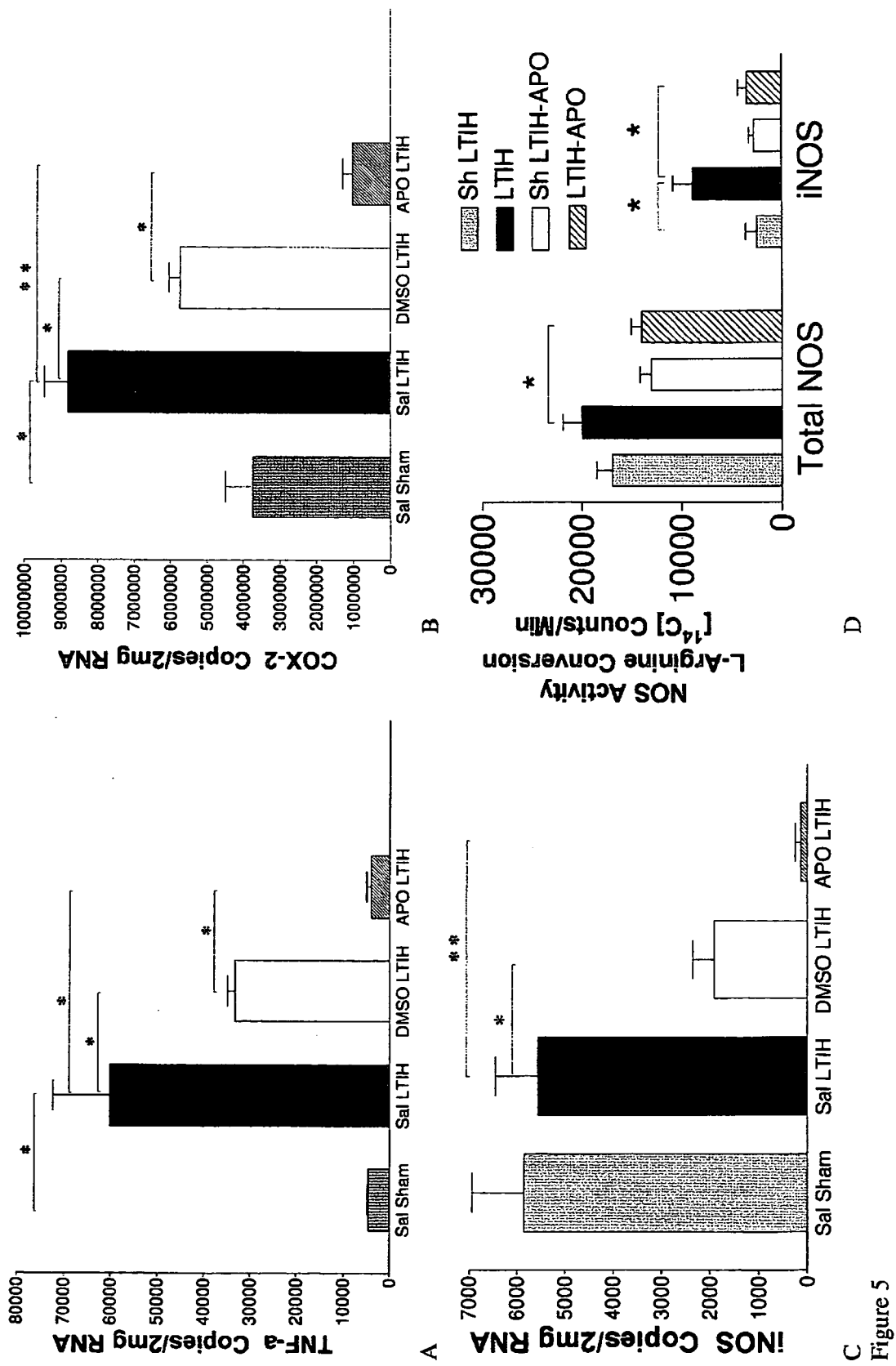
FIG. 5. NADPH oxidase inhibition confers resistance to the long-term intermittent hypoxia (LTIH) proinflammatory response. Proinflammatory gene expression was measured in micropunches in the lateral basal forebrains in $gp91^{phox}$ wild type controls ($gp91^{phox}$ WT, n=10) and $gp91^{phox}$ null mice ($gp91^{phox}$ null, n=10) for A, TNF-a; B, COX-2 and C, iNOS mRNA copies/2□g total RNA. D. Total NOS activity (left columns), measured as L-arginine conversion of [$^{14}$C] L-arginine to L-citrulline and iNOS activity (right columns) was measured using 5 mm S-Ethyl-N-[4-trifluoromethyl)phenyl] isothiourea (ETPI) added to homogenates (12). Apocynin prevents the anticipated LTIH increase in iNOS activity.
Figure 6:
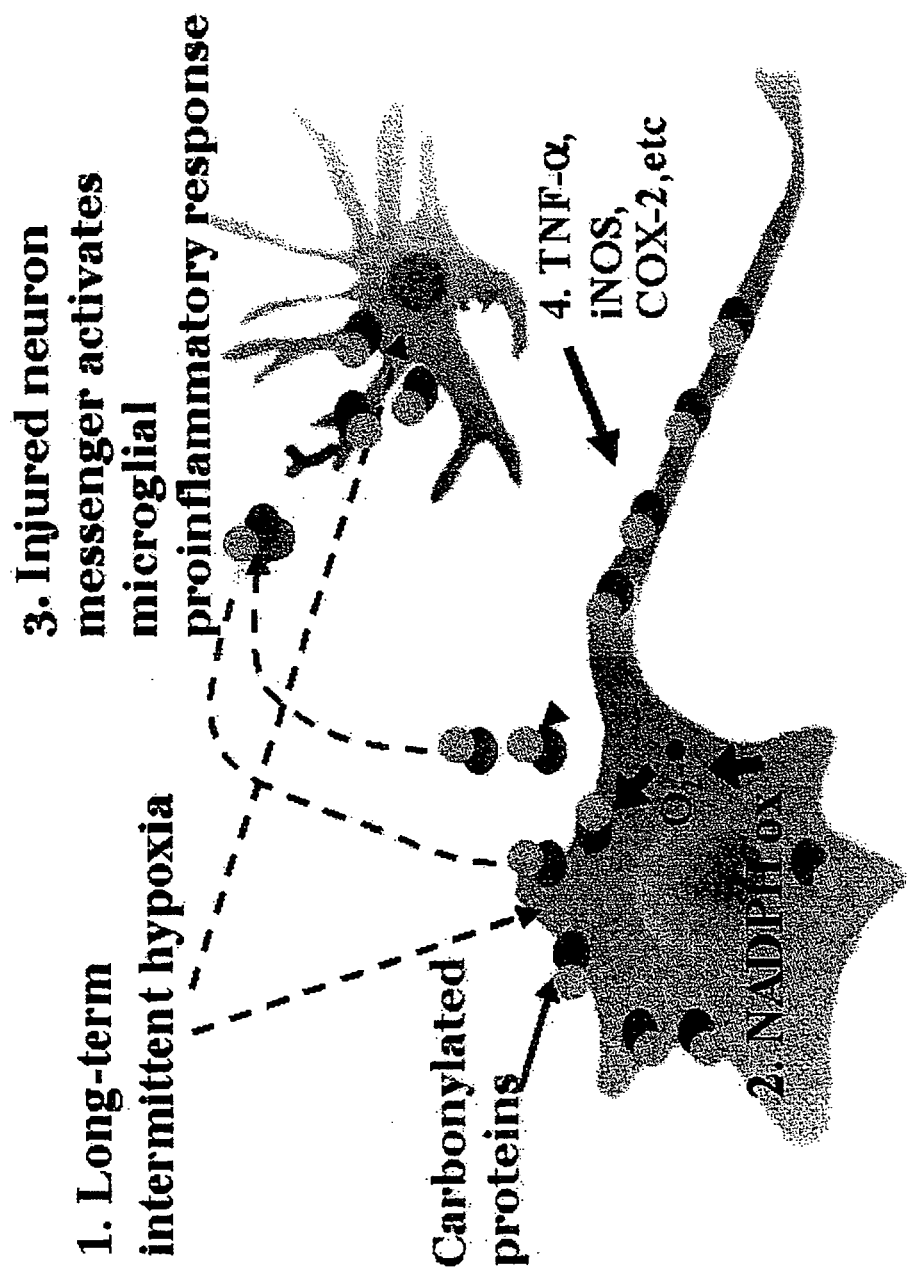
FIG. 6. Proposed model of long-term intermittent hypoxia-induced neural injury. Neurons with NADPH oxidase activation responses to long-term intermittent hypoxia (LTIH) are at increased risk of oxidative injury. The present study shows that LTIH activates NADPH oxidase in select neurons, including at least some groups of wake-active neurons. The mechanisms of LTIH activation of NADPH oxidase are unknown. However, NADPH oxidase activation and production of superoxide radical ($O_2$—.) manifest, in part, as increased irreversible and progressive carbonylation injury to proteins. Redox alterations in surface proteins or secreted proteins activate adjacent microglia. Activation of microglia results in further increase of NADPH oxidase but also a proinflammatory response including iNOS, COX-2 and TNF-α. INOS production of nitric oxide combined with adjacent $O_2$—. molecules will result in peroxynitrite formation for lipid peroxidation of membranes. This lipid peroxidation of neural membranes and released COX-2 and TNF-α promote a vicious cycle of continued oxidative and inflammatory injury persisting after normalization of ambient oxygen tensions. NADPH oxidase blockade prevents all injuries described.

NADPH Oxidase Inhibition Throughout LTIH Prevents the LTIH Proinflammatory Response LTIH increases proinflammatory gene expression (TNF-α and COX-2) in the cortex, hippocampus and wake-active regions, and this response is still present 2 weeks into recovery. To determine whether proinflammatory response is NADPH oxidase dependent, we compared gene responses to LTIH in mice treatment with apocynin, vehicle or saline to sham LTIH treated responses in a representative wake-active region, the lateral basal forebrain (FIG. 4A) Consistent with previous findings, the group treated with saline throughout LTIH (n=6), relative to sham LTIH (n=6) exhibited large increases in TNF-α (>10-fold increase, t=4.1, p<0.01, FIG. 5A) and in COX-2 mRNA (140% increase, t=6.6, p<0.001, FIG. 4B). Treatment with apocynin throughout LTIH completely prevented the increases in TNF-α gene expression (FIG. 5A). Specifically, LTIH TNF-α levels, in apocynin-treated mice did not differ from sham LTIH values, t=0.7, N.S. Apocynin treatment during LTIH reduced the TNF-α response to 7% of the saline LTIH response, t=4.8, p<0.001. DMSO (vehicle alone) treatment during LTIH reduced the LTIH response to 35% of the expected (t=2.8, p<0.05); vehicle treatment, however, was less effective than apocynin in reducing the LTIH TNF-α response (Apo vs. DMSO, 73% lower, t=2.8, p<0.05). Apocynin therapy had similar effects on the LTIH COX-2 gene response. Treatment with the apocynin in DMSO vehicle completely blocked the LTIH COX-2 response in the lateral basal forebrain (t=10.2, p<0.0001) to below the sham LTIH gene expression (65% reduction relative to sham LTIH, t=3.5, p<0.05, FIG. 5B). Treatment with the DMSO vehicle also had some effect in reducing the LTIH gene response reduced the LTIH gene responses in the lateral basal forebrain, when compared with saline treated LTIH (75% reduction, t=8.6, p<0.01). Thus, systemic apocynin was extremely effective in preventing the LTIH proinflammatory gene response. DMSO, the vehicle used for apocynin had some effect on blunting the TNF-α and COX-2 increased expression, but was not as effective as apocynin.

LTIH has been shown to have little effect on the iNOS gene response in wake active regions but has a significant effect on iNOS activity. Thus, we sought to determine whether apocynin therapy affected iNOS gene response and whether inhibition of NADPH oxidase blocked the LTIH effect on iNOS activity. iNOS gene copies were reduced in both the DMSO (66% reduction in iNOS mRNA, p<0.01) and apocynin groups (94% reduction in iNOS mRNA, p<0.001, FIG. 5C), with markedly reduced gene expression in the apocynin group, relative to the vehicle group (t=8.3, p<0.001). Lateral basal forebrain iNOS activity was compared in mice treated with or without apocynin throughout LTIH (FIG. 5D). Apocynin therapy, relative to saline therapy had no effect on baseline (sham LTIH) iNOS activity. In contrast, apocynin prevented the LTIH increase in iNOS activity, resulting in a large reduction (60%) in iNOS activity in apocynin treated vs. untreated mice (t=3.4, p<0.05), so that apocynin-treated LTIH iNOS activity did not differ from sham LTIH iNOS activity levels in the lateral basal forebrain. Administration of the apocynin vehicle, DMSO, throughout LTIH resulted in higher iNOS activity than apocynin therapy, t=2.8, p<0.05. Thus, apocynin therapy throughout LTIH prevented the expected increase in iNOS activity.

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A method for treating a hypersomnolence or sleepiness associated with Obstructive Sleep Apnea (OSA) hypopnea syndrome in a subject having OSA, comprising administering a therapeutically effective amount of a composition comprising an NADPH oxidase inhibitor to a subject in need thereof, wherein said method increases sleep latency in a healthy subject relative to a subject having OSA without impairing sleep loss-related sleepiness, thereby treating said hypersomnolence or sleepiness.

2. The method of claim 1, wherein said NADPH oxidase inhibitor is apocynin.

3. A method for treating a cardiovascular morbidity resulting from Obstructive Sleep Apnea (OSA) hypopnea syndrome, comprising administering a therapeutically effective amount of a composition comprising an NADPH oxidase inhibitor to a subject in need thereof, wherein said inhibitor reverses increases in proinflammatory gene expression in the cortex, hippocampus, and wake-active regions that result from OSA, thereby treating said cardiovascular morbidity.

4. The method of claim 1, wherein said composition further comprises a siRNA targeted to $p47^{phox}$ subunit of NADPH oxidase.

5. The method of claim 1, further comprising the step of coadministrering to said subject a COX-2 inhibitor.

6. The method of claim 1, wherein said subject is a snorer.

7. The method of claim 3, wherein said proinflammatory gene is tumor necrosis factor-alpha (TNF-α), Cyclooxygenase-2 (COX-2), or both.

* * * * *